(12) United States Patent
Baek et al.

(10) Patent No.: US 10,786,662 B2
(45) Date of Patent: Sep. 29, 2020

(54) METHOD OF MANUFACTURING MICRONEEDLE AND MICRONEEDLE MANUFACTURED THEREBY

(71) Applicant: QuadMedicine, Seongnam-si, Gyeonggi-do (KR)

(72) Inventors: Seung Ki Baek, Seoul (KR); Myun Hwan Ahn, Namyangju-si (KR); Sun Young Baek, Seoul (KR)

(73) Assignee: QuadMedicine, Seongnam-si (KR)

( * ) Notice: Subject to any disclaimer, the term of this patent is extended or adjusted under 35 U.S.C. 154(b) by 0 days.

(21) Appl. No.: 15/863,318

(22) Filed: Jan. 5, 2018

(65) Prior Publication Data

US 2018/0185625 A1 Jul. 5, 2018

(30) Foreign Application Priority Data

Jan. 5, 2017 (KR) .................. 10-2017-0001777

(51) Int. Cl.
*A61M 37/00* (2006.01)
*B29C 33/42* (2006.01)
*B29C 39/02* (2006.01)
*B81C 1/00* (2006.01)
*B29L 31/00* (2006.01)

(52) U.S. Cl.
CPC ....... *A61M 37/0015* (2013.01); *B29C 33/424* (2013.01); *B29C 39/02* (2013.01); *A61M 2037/0053* (2013.01); *B29L 2031/756* (2013.01); *B29L 2031/7544* (2013.01); *B81C 1/00206* (2013.01)

(58) Field of Classification Search
CPC .................................................. A61M 37/00
See application file for complete search history.

(56) References Cited

U.S. PATENT DOCUMENTS

| | | | |
|---|---|---|---|
| 2004/0049150 A1* | 3/2004 | Dalton | A61B 17/205 604/46 |
| 2008/0213461 A1* | 9/2008 | Gill | A61K 9/0021 427/2.3 |
| 2012/0130306 A1* | 5/2012 | Terahara | A61K 9/0021 604/46 |

(Continued)

FOREIGN PATENT DOCUMENTS

| | | |
|---|---|---|
| JP | 5879927 B2 | 3/2016 |
| KR | 2003-0077473 A | 10/2003 |
| KR | 10-2014-0084042 A | 7/2014 |

(Continued)

OTHER PUBLICATIONS

English Machine Translation of KR 10-2016-0058261 (Year: 2016).*
Korean Office Action of 10-2017-001777 filed Jan. 31, 2017.

*Primary Examiner* — Dah-Wei D. Yuan
*Assistant Examiner* — Andrew J Bowman
(74) *Attorney, Agent, or Firm* — Sughrue Mion, PLLC

(57) ABSTRACT

A method of manufacturing a microneedle according to the present disclosure includes a step of preparing a microneedle; a step of cooling the microneedle; and a step of inducing an endothermic reaction of the cooled microneedle, and coating the cooled microneedle with an active ingredient at least once. In accordance with such a configuration, coatability of the active ingredient can be improved due to an endothermic reaction without a separate drying process, thereby providing superior medication.

14 Claims, 6 Drawing Sheets

(56) References Cited

U.S. PATENT DOCUMENTS

2014/0128811 A1   5/2014   Ferguson et al.
2019/0046778 A1*  2/2019   Jin .......................... A61K 9/00

FOREIGN PATENT DOCUMENTS

| KR | 10-1610598    | B1 |   | 4/2016 |
| KR | 10-2016-0058261 | A |   | 5/2016 |
| KR | 20160058261   | A | * | 5/2016 |

\* cited by examiner (a)

(b)

(a)

(b)

US 10,786,662 B2

METHOD OF MANUFACTURING MICRONEEDLE AND MICRONEEDLE MANUFACTURED THEREBY

CROSS-REFERENCE TO RELATED APPLICATION

This application claims the priority benefit of Korean Patent Application No. 10-2017-0001777, filed on Jan. 5, 2017 in the Korean Intellectual Property Office, the disclosure of which is incorporated herein by reference.

BACKGROUND OF THE DISCLOSURE

Field of the Disclosure

The present disclosure relates to a method of manufacturing a microneedle and a microneedle manufactured thereby, more particularly to a method of manufacturing a microneedle capable of effectively applying a predetermined amount of drug due to increase in a coating rate of an active ingredient, and a microneedle manufactured thereby.

Description of the Related Art

Various drug delivery technologies, such as oral delivery, injection, transdermal delivery, and mucosal delivery, have been used. Thereamong, transdermal drug delivery technology, which is a technology of delivering drugs through the skin using patches, creams, etc., has advantages in that it is not affected by intestinal metabolism and continuous drug delivery may be accomplished by using patches.

As general transdermal drug delivery methods, there are a passive transdermal drug delivery system and an active transdermal drug delivery system. A passive transdermal drug delivery system, which is a passive method depending upon physicochemical properties of a drug, is characterized by spreading a cream, a patch, an ointment, etc. on the skin. Meanwhile, such a passive transdermal drug delivery method has a limitation in that the molecular weight of a drug capable of being delivered through the skin is 500 Da or less.

In addition, in the case of an active transdermal drug delivery method, an effective ingredient is delivered by physically penetrating the stratum corneum, which has a thickness of 10 µm, with a microneedle so as to overcome limitation in penetrating the skin. In such active transdermal drug delivery, a solid cream-type microneedle, a microneedle coated with an effective ingredient, a microneedle melting in water, a hollow microneedle smaller than conventional needles, and the like are used.

A solid cream-type microneedle has a limitation in that a drying process is essential upon coating a microneedle with an active ingredient. A microneedle that melts in water has a limitation in that, upon coating the microneedle with a substance having the same properties as the microneedle, the microneedle and the substance are bound to each other, whereby a tip end thereof is blunted and thus mechanical strength thereof is lost. Accordingly, various research has been continuously carried out to increase coatability of an active ingredient on a microneedle such that a predetermined amount of drug permeates into the skin.

RELATED DOCUMENTS

Patent Documents (Patent Document 1) Japanese Patent No. 5879927
(Patent Document 2) US Patent Application Publication No. 2014-0128811

SUMMARY OF THE DISCLOSURE

Therefore, the present disclosure has been made in view of the above problems, and it is one object of the present disclosure to provide a microneedle capable of providing superior medication due to a simple manufacturing process and improved coatability of an active ingredient by an endothermic reaction, and a method of manufacturing the microneedle.

In accordance with an aspect of the present disclosure, the above and other objects can be accomplished by the provision of a method of manufacturing a microneedle, the method including preparing a water-soluble microneedle; cooling the water-soluble microneedle; and inducing an endothermic reaction of the cooled water-soluble microneedle, and coating the cooled water-soluble microneedle with a water-soluble active ingredient at least once.

In accordance with an aspect of the present disclosure, the preparing may include preparing a mold having a plurality of tip grooves; supplying a chemical liquid including at least a portion of a raw material or a biodegradable polymer ingredient to the mold to mold the microneedle; and removing the mold from the microneedle.

In accordance with an aspect of the present disclosure, the mold may include a polydimethylsiloxane (PDMS) mold and at least one of polyurethane, a metal, a biocompatible aluminum material, a water-soluble polymer, a lipophilic polymer, and an amphiphilic polymer, wherein the lipophilic polymer and the amphiphilic polymer include at least one of hydroxypropyl cellulose (HPC), hydroxypropyl methyl cellulose (HPMC), polycaprolactone (PCL), polyglycolide (PGA), polylactic acid (PLA), a polylactide-glycolide (PLGA) copolymer, polyvinylpyrrolidone (PVP), polyethylene glycol (PEG), polyethylene oxide (PEO), polypropylene oxide (PPO), poly(vinyl methyl ether) (PVME), poly (methyl acrylate) (PMA), propylene glycol, polyesteramide, polybutyric acid, acrylamide (acrylic amide), acrylic acid, hyaluronic acid (HA), and gelatin.

In accordance with an aspect of the present disclosure, in the supplying, the microneedle may be molded through centrifugation and a polymer melting process after injecting the chemical liquid including the raw material in a low or high viscosity state into the mold.

In accordance with an aspect of the present disclosure, the chemical liquid may be formed of a biocompatible material and a water-soluble additive.

In accordance with an aspect of the present disclosure, the biocompatible material may include at least one of carboxymethyl cellulose (CMC), hyaluronic acid (HA), alginic acid, pectin, carrageenan, chondroitin sulfate, dextran sulfate, chitosan, polylysine, carboxymethyl chitin, fibrin, agarose, pullulan, polyanhydride, polyorthoester, polyetherester, polyesteramide, polybutyric acid, poly(valeric acid), polyacrylate, an ethylene-vinyl acetate polymer, acryl-substituted cellulose acetate, polyvinyl chloride, polyvinyl fluoride, polyvinyl imidazole, chlorosulphonate polyolefins, polyethylene oxide, polyvinylpyrrolidone (PVP), hydroxypropyl methyl cellulose (HPMC), ethyl cellulose (EC), hydroxypropyl cellulose (HPC), carboxymethyl cellulose, cyclodextrin, maltose, lactose, trehalose, cellobiose, isomaltose, turanose, and lactulose, or one or more of a copolymer of monomers forming this polymer and cellulose.

In accordance with an aspect of the present disclosure, the water-soluble additive may include at least one of trehalose, oligosaccharide, sucrose, maltose, lactose, cellobiose, hyaluronic acid, alginic acid, pectin, carrageenan, chondroitin sulfate, dextran sulfate, chitosan, polylysine, collagen, gelatin, carboxymethyl chitin, fibrin, agarose, polyvinylpyrrolidone (PVP), polyethylene glycol (PEG), polymethacrylate, hydroxypropyl methyl cellulose (HPMC), ethyl cellulose (EC), hydroxypropyl cellulose (HPC), carboxymethyl cellulose, cyclodextrin, and gentiobiose.

In accordance with an aspect of the present disclosure, in the cooling, the microneedle may be cooled by at least one rapid cooling method of a screw method, a piston method, a mono-pump method, a time-pressure method, a valve method, a spray method, a piezo method, and an air-solenoid method.

In accordance with an aspect of the present disclosure, in the cooling, at least one cooling substance of liquid nitrogen, tetrafluoroethane, a Peltier element cooling fan, dry ice, carbon tetrachloride, trichlorofluoromethane, dichlorodifluoromethane, bromochlorodifluoromethane, dibromodifluoromethane, chlorotrifluoromethane, bromotrifluoromethane, tetrafluoromethane, chloroform, dichlorofluoromethane, chlorodifluoromethane, bromodifluoromethane, trifluoromethane, dichloromethane, chlorofluoromethane, methylene fluoride (difluoromethane), methyl chloride (chloromethane), methyl fluoride (fluoromethane), methane, hexachloroethane, pentachlorofluoroethane, tetrachlorodifluoroethane, trichlorotrifluoroethane, dichlorotetrafluoroethane (1,2-dichlorotetrafluoroethane), dibromotetrafluoroethane, chloropentafluoroethane, hexafluoroethane, pentachloroethane, dichlorotrifluoroethane (2,2-dichloro-1,1,1-trifluoroethane), chlorotetrafluoroethane, pentafluoroethane, tetratrifluoroethane, tetrafluoroethane, trichloroethane (methyl chloroform), dichlorofluoroethane (1,1-dichloro-1-fluoroethane), chlorodifluoroethane, trifluoroethane, dichloroethane, difluoroethane, chloroethane, ethane, dichlorohexafluoropropane, liquid helium, and liquid oxygen, or a combination thereof may be used.

In accordance with an aspect of the present disclosure, in the cooling, a temperature of the microneedle may be adjusted by immersing the microneedle in liquid nitrogen.

In accordance with an aspect of the present disclosure, in the coating, the microneedle cooled may be coated with the active ingredient by at least one method of an immersion coating method, an electro-spinning coating method, an ultrasonic coating method, an atomization coating method, and a non-contact spray coating method.

In accordance with an aspect of the present disclosure, the active ingredient may be provided in a liquid state based on water and a solvent, and may be included in a ratio of 0.1% to 30% based on the drug.

In accordance with an aspect of the present disclosure, the cooling and the coating may be carried out at under a relative humidity of less than 50% under a vacuum or dry air condition.

In accordance with an aspect of the present disclosure, in the coating, the water-soluble microneedle may be coated, in a multilayer structure, with two or more active ingredients having the same solubility In accordance with an aspect of the present disclosure, in the coating, the active ingredient may be coated up to one fifth or more of the height of the microneedle from an upper end of the microneedle.

In accordance with an aspect of the present disclosure, in the coating, a coating agent including a thickening agent, a biodegradable polymer resin, a water-soluble substance, and an active ingredient to be delivered to skin tissue may be used.

In accordance with an aspect of the present disclosure, the thickening agent may include at least one of locust bean gum, rennet casein, dammer resin, glucosamine, glucomannan, guar gum, ghatti gum, carbomer, povidone, glycerin, carboxymethyl cellulose (CMC), hyaluronic acid, alginic acid, pectin, carrageenan, chondroitin sulfate, dextran sulfate, alginic acid, chitosan, karaya gum, polylysine, carboxymethyl chitin, fibrin, agarose, pullulan, polyanhydride, gellan gum, chitin, polyorthoester, microfibrillated, furcelleran, tragacanth gum, polyetherester, polyester amide, polybutyric acid, curdlan, polyvaleric acid, xanthan gum, polyacrylate, an ethylene-vinyl acetate polymer, acryl-substituted cellulose acetate, polyvinyl chloride, polyvinyl fluoride, tara gum, arabic gum, polyvinyl imidazole, psyllium seed gum, chlorosulphonate polyolefins, polyethylene oxide, polyvinyl pyrrolidone (PVP), chlorosulphonate polyolefins, hydroxypropyl methyl cellulose (HPMC), ethyl cellulose (EC), hydroxypropyl cellulose (HPC), carboxymethyl cellulose, cyclodextrin, maltose, lactose, trehalose, cellobiose, isomaltose, turanose, and lactulose, or at least one of a copolymer of monomers forming this polymer and cellulose.

In accordance with an aspect of the present disclosure, the active ingredient may include at least one of α-interferon, β-interferon related to multiple sclerosis, interferon gamma, interleukin-1 alpha and beta, interleukin-3, interleukin-4, interleukin-6, interleukin-2, erythropoietin, follitropin β, follitropin α, G-CSF, GM-CSF, human chorionic gonadotropin, signal transduction proteins, adherent proteins, luteinizing hormone, salmon calcitonin, glucagon, structural proteins, regulatory proteins, toxin proteins, cytokines, transcriptional regulatory factors, glucagon, blood coagulation factors, vaccines, enzyme inhibitors, a GNRH antagonist, insulin, human growth hormone, erythropoietin, filgrastin, heparin, low-molecular-weight heparin, and somatotropin.

In accordance with an aspect of the present disclosure, the water-soluble substance may be at least one of trehalose, oligosaccharide, sucrose, maltose, lactose, cellobiose, hyaluronic acid, alginic acid, pectin, carrageenan, chondroitin sulfate, dextran sulfate, chitosan, polylysine, collagen, gelatin, carboxymethyl chitin, fibrin, agarose, polyvinylpyrrolidone (PVP), polyethylene glycol (PEG), polymethacrylate, hydroxypropyl methyl cellulose (HPMC), ethyl cellulose (EC), hydroxypropyl cellulose (HPC), carboxymethyl cellulose, cyclodextrin, and gentiobiose.

In accordance with an aspect of the present disclosure, the microneedle may include a plurality of tips having a conical shape or a polygonal pyramid shape.

In accordance with an aspect of the present disclosure, the method may further include a step of evaporating a solvent from the coated microneedle, and waterproof-coating the microneedle such that the coated surface thereof is not affected by a solution.

In accordance with an aspect of the present disclosure, in the waterproof-coating, an end portions or entire surface of the microneedle may be coated with a waterproofing agent including a mineral-based substance or a lipid-based material by at least one of a dip-coating method, an atomization coating method, an electro-spinning coating method, and an ultrasonic coating method.

In accordance with an aspect of the present disclosure, the waterproofing agent may include at least one of beeswax, oleic acid, soy fatty acid, castor oil, phosphatidylcholine, vitamin E (d-α-tocopherol/Vitamin E), corn oil mono-di-tridiglycerides, cottonseed oil, olive oil, peanut oil, peppermint oil, safflower oil, sesame oil, soybean oil, hydrogenated vegetable oils, hydrogenated soybean oil, capric triglycerides (caprylic/capric triglycerides derived from coconut oil or palm seed oil) and phosphatidylcholine, or may be formed of a mixture thereof.

In accordance with a preferred embodiment of the present disclosure, the microneedle is manufactured through the following sequential steps: a step of preparing a microneedle; a step of cooling the microneedle; and a step of inducing an endothermic reaction of the cooled microneedle, and coating the cooled microneedle with an active ingredient at least once.

BRIEF DESCRIPTION OF THE DRAWINGS

The above and other objects, features and other advantages of the present disclosure will be more clearly understood from the following detailed description taken in conjunction with the accompanying drawings, in which.

DETAILED DESCRIPTION OF THE DISCLOSURE

Hereinafter, a preferred embodiment of the present disclosure is described with reference to the accompanying drawings.

Figure 1:
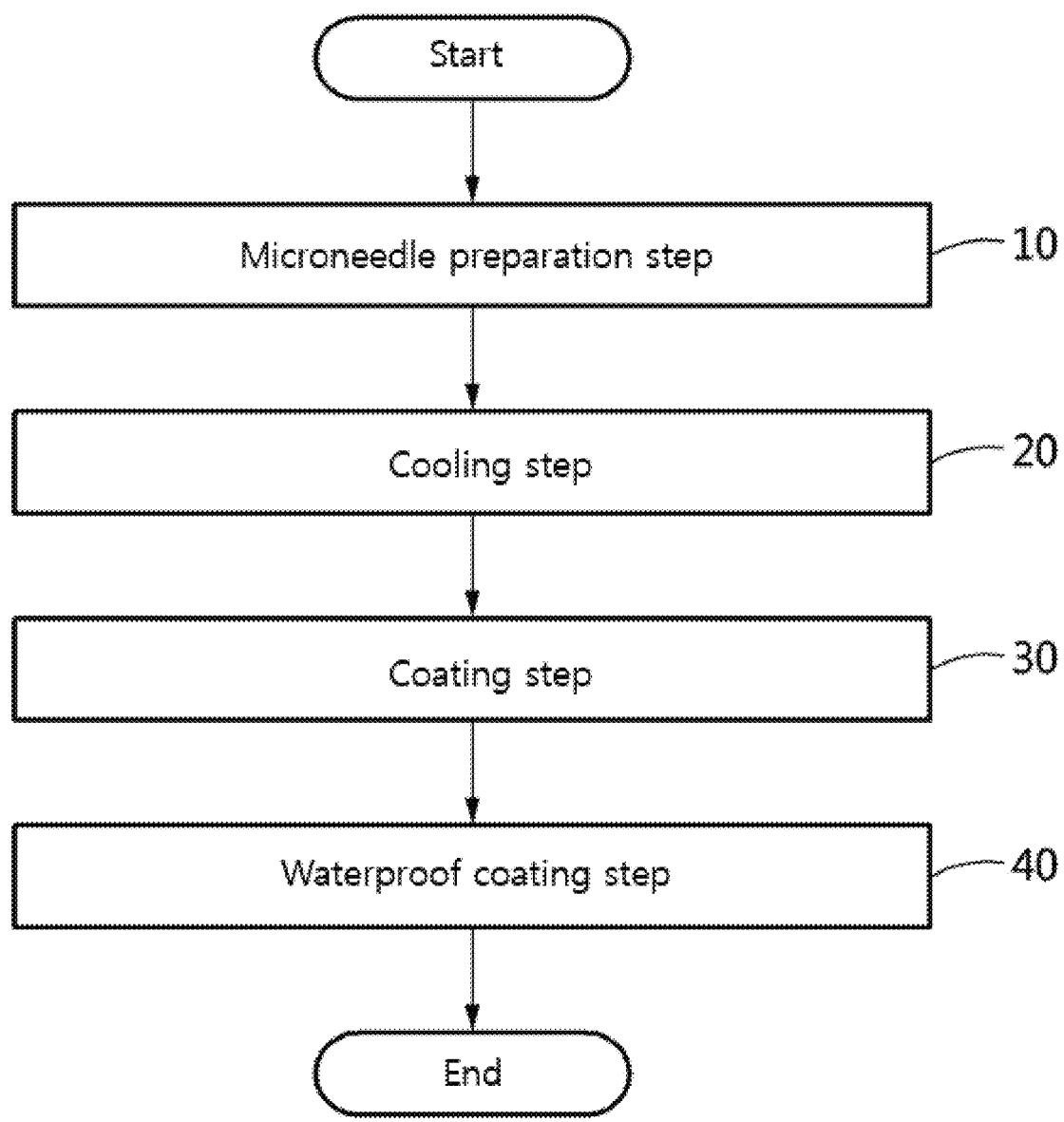
FIG. 1 is a flowchart schematically illustrating a procedure of a method of manufacturing a microneedle according to a preferred embodiment of the present disclosure.

FIG. 1 schematically illustrates a method of manufacturing a microneedle 1 (see FIG. 2) according to a preferred embodiment of the present disclosure.

Referring to FIG. 1, the method of manufacturing the microneedle 1 includes a microneedle preparation step 10, the cooling step 20, a coating step 30, and a waterproof coating step 40.

Figure 2:
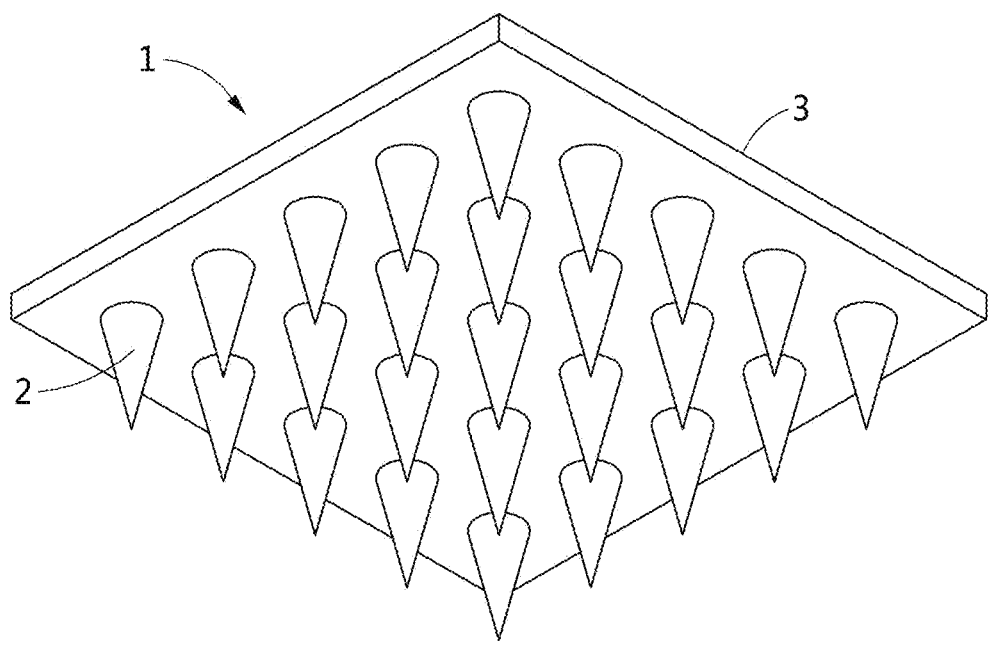
FIG. 2 is a perspective view schematically illustrating a microneedle manufactured according to the method of FIG. 1.

In the microneedle preparation step 10, the microneedle 1 including a plurality of tips 2 and a base 3 is prepared, as illustrated in FIG. 2.

The tips 2 have a sharp shape such that end portions thereof may easily penetrate the skin of a human body or an animal. Here, the tips 2 are exemplified as having a substantially conical shape or polygonal pyramid shape. In addition, the plurality of tips 2 is arranged in multiple rows. The shape and number of the tips 2 are not limited to the illustrated embodiment.

The base 3, which supports the tips 2 and is a body of the microneedle 1, is a kind of patch attached to the skin while supporting the tips 2.

For reference, the tips 2 have a length of about 50 μm to 2000 μm, preferably a length of 90 μm to 800 μm. Preferably, the tips 2 extend from the base 3.

Figure 3:
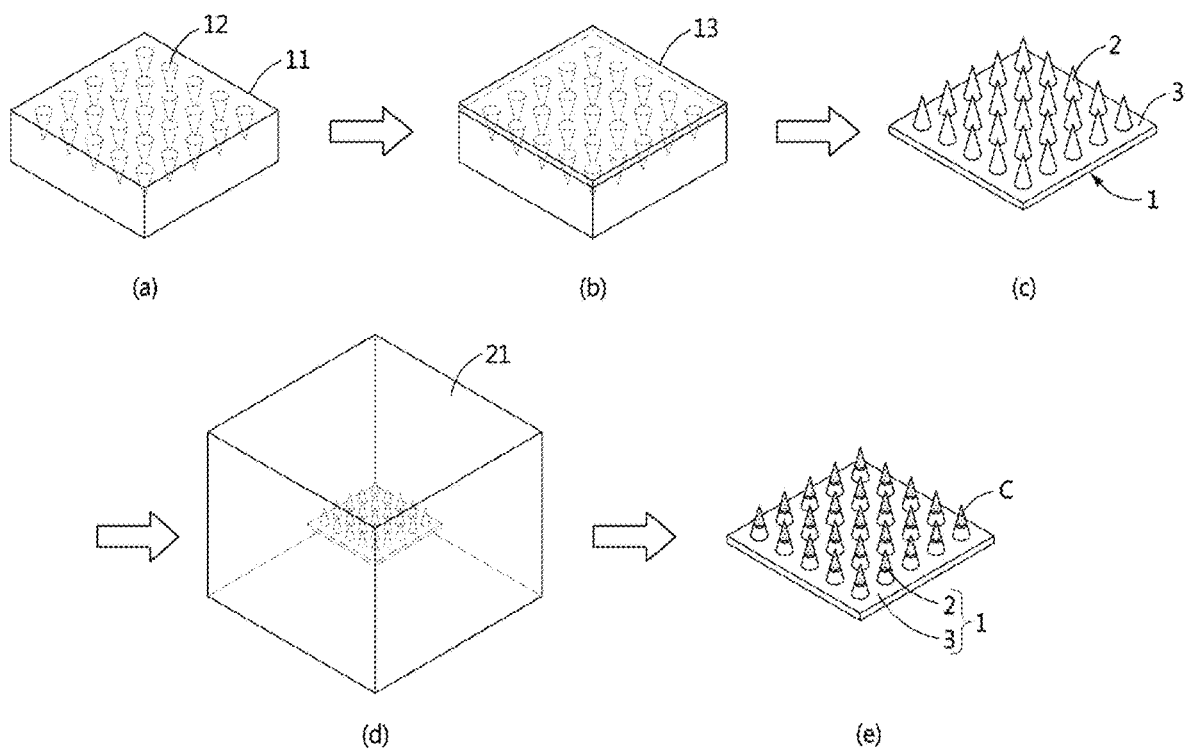
FIG. 3 is a drawing illustrating steps of manufacturing a microneedle according to the method of FIG. 1.

In the microneedle 1 preparation step 10, the microneedle 1 is prepared through molding, as illustrated in (a) to (c) of FIG. 3.

More particularly, as illustrated in (a) of FIG. 3, a step of preparing a mold 11 having a plurality of tip grooves 12 corresponding to shapes of the tips 2 of the microneedle 1 is included. As illustrated in (b) of FIG. 3, a chemical liquid 13 including a raw material or a biodegradable polymer ingredient is supplied into the prepared mold 11, and dispensed into the tip grooves 12 to be filled. The chemical liquid 13 filled in the mold 11 is solidified, thereby molding the microneedle 1. The molded microneedle 1 is separated from the mold 11, as illustrated in (c) of FIG. 3. Here, the chemical liquid 13 including the raw material is injected in a low or high viscosity state into the mold 11, and then is solidified through centrifugation and a polymer melting process to mold the water-soluble microneedle 1.

Here, the mold 11 includes a structure including a polydimethylsiloxane (PDMS) mold and at least one of polyurethane, a metal, a biocompatible aluminum material, a water-soluble polymer, a lipophilic polymer, and an amphiphilic polymer. Here, the lipophilic polymer and the amphiphilic polymer are exemplified as including at least one of hydroxypropyl cellulose (HPC), hydroxypropyl methyl cellulose (HPMC), polycaprolactone (PCL), polyglycolide (PGA), polylactic acid (PLA), a polylactide-glycolide (PLGA) copolymer, polyvinylpyrrolidone (PVP), polyethylene glycol (PEG), polyethylene oxide (PEO), polypropylene oxide (PPO), poly(vinyl methyl ether) (PVME), poly (methyl acrylate) (PMA), propylene glycol, polyesteramide, polybutyric acid, acrylamide (acrylic amide), acrylic acid, hyaluronic acid (HA), and gelatin.

In addition, the chemical liquid 13 injected into the mold 11 is formed of a biocompatible material and a water-soluble additive. Here, the biocompatible material includes at least one of carboxymethyl cellulose (CMC), hyaluronic acid (HA), alginic acid, pectin, carrageenan, chondroitin sulfate, dextran sulfate, chitosan, polylysine, carboxymethyl chitin, fibrin, agarose, pullulan, polyanhydride, polyorthoester, polyetherester, polyesteramide, polybutyric acid, poly(valeric acid), polyacrylate, an ethylene-vinyl acetate polymer, acryl-substituted cellulose acetate, polyvinyl chloride, polyvinyl fluoride, polyvinyl imidazole, chlorosulphonate polyolefins, polyethylene oxide, polyvinylpyrrolidone (PVP), hydroxypropyl methyl cellulose (HPMC), ethyl cellulose (EC), hydroxypropyl cellulose (HPC), carboxymethyl cellulose, cyclodextrin, maltose, lactose, trehalose, cellobiose, isomaltose, turanose, and lactulose, or one or more of a copolymer of monomers forming this polymer and cellulose.

The water-soluble additive includes at least one of trehalose, oligosaccharide, sucrose, maltose, lactose, cellobiose, hyaluronic acid, alginic acid, pectin, carrageenan, chondroitin sulfate, dextran sulfate, chitosan, polylysine, collagen, gelatin, carboxymethyl chitin, fibrin, agarose, polyvinylpyrrolidone (PVP), polyethylene glycol (PEG), polymethacrylate, hydroxypropyl methyl cellulose (HPMC), ethyl cellulose (EC), hydroxypropyl cellulose (HPC), carboxymethyl cellulose, cyclodextrin, and gentiobiose.

The microneedle 1 prepared as described above is cooled (step 20). In the cooling step 20, the microneedle 1 is put into a cooling chamber 21 sealed as illustrated in (d) of FIG. 3, and then cooling is performed. More particularly, in the cooling step 20, the microneedle 1 is cooled by at least one rapid cooling method of a screw method, a piston method, a mono-pump method, a time-pressure method, a valve method, a spray method, a piezo method, and an air-solenoid method. In addition, in the cooling step 20, the microneedle 1 may be cooled by immersing the same in a cooling substance capable of inducing an endothermic reaction.

Here, the cooling substance may be at least one of liquid nitrogen, tetrafluoroethane, a Peltier element cooling fan, dry ice, carbon tetrachloride, trichlorofluoromethane, dichlorodifluoromethane, bromochlorodifluoromethane, dibromodifluoromethane, chlorotrifluoromethane, bromotrifluoromethane, tetrafluoromethane, chloroform, dichlorofluoromethane, chlorodifluoromethane, bromodifluoromethane, trifluoromethane, dichloromethane, chlorofluoromethane, methylene fluoride (difluoromethane), methyl chloride (chloromethane), methyl fluoride (fluoromethane), methane, hexachloroethane, pentachlorofluoroethane, tetrachlorodifluoroethane, trichlorotrifluoroethane, dichlorotetrafluoroethane (1,2-dichlorotetrafluoroethane), dibromotetrafluoroethane, chloropentafluoroethane, hexafluoroethane, pentachloroethane, dichlorotrifluoroethane (2,2-dichloro-1,1,1-trifluoroethane), chlorotetrafluoroethane, pentafluoroethane, tetratrifluoroethane, tetrafluoroethane, trichloroethane (methyl chloroform), dichlorofluoroethane (1,1-dichloro-1-fluoroethane), chlorodifluoroethane, trifluoroethane, dichloroethane, difluoroethane, chloroethane, ethane, dichlorohexafluoropropane, liquid helium, and liquid oxygen, or a combination thereof. In addition, the cooling substance may include liquid nitrogen.

The cooling step 20 is a step of appropriately adjusting temperature of the microneedle 1 to coat the microneedle 1 with an effective drug. That is, the cooling step 20 induces an endothermic reaction by cooling the microneedle 1 before the coating step 30 described below, thereby inducing drying and safe and rapid coating with a drug having solubility.

In the coating step 30, as illustrated in (e) of FIG. 3, the cooled microneedle 1 is coated with the coating agent C including an active ingredient due to an endothermic reaction of the microneedle 1. In the coating step 30, the cooled microneedle 1 is coated with the coating agent C by at least one method of an immersion coating method, an electro-spinning coating method, an ultrasonic coating method, an atomization coating method, and a non-contact spray coating method.

The coating agent C may include a thickening agent, a biodegradable polymer resin, a water-soluble substance, and an active ingredient to be delivered to skin tissue. The thickening agent includes at least one of locust bean gum, rennet casein, dammer resin, glucosamine, glucomannan, guar gum, ghatti gum, carbomer, povidone, glycerin, carboxymethyl cellulose (CMC), hyaluronic acid, alginic acid, pectin, carrageenan, chondroitin sulfate, dextran sulfate, alginic acid, chitosan, karaya gum, polylysine, carboxymethyl chitin, fibrin, agarose, pullulan, polyanhydride, gellan gum, chitin, polyorthoester, microfibrillated, furcelleran, tragacanth gum, polyetherester, polyester amide, polybutyric acid, curdlan, polyvaleric acid, xanthan gum, polyacrylate, an ethylene-vinyl acetate polymer, acryl-substituted cellulose acetate, polyvinyl chloride, polyvinyl fluoride, tara gum, arabic gum, polyvinyl imidazole, psyllium seed gum, chlorosulphonate polyolefins, polyethylene oxide, polyvinyl pyrrolidone (PVP), chlorosulphonate polyolefins, hydroxypropyl methyl cellulose (HPMC), ethyl cellulose (EC), hydroxypropyl cellulose (HPC), carboxymethyl cellulose, cyclodextrin, maltose, lactose, trehalose, cellobiose, isomaltose, turanose, and lactulose, or at least one of a copolymer of monomers forming this polymer and cellulose. That is, the composition of the active ingredient is partially similar to that of the chemical liquid 13 constituting the microneedle 1, and the chemical liquid 13 may include at least portion of the active ingredient.

In addition, the active ingredient may include at least one of α-interferon, β-interferon related to multiple sclerosis, interferon gamma, interleukin-1 alpha and beta, interleukin-3, interleukin-4, interleukin-6, interleukin-2, erythropoietin, follitropin (3, follitropin α, G-CSF, GM-CSF, human chorionic gonadotropin, signal transduction proteins, adherent proteins, luteinizing hormone, salmon calcitonin, glucagon, structural proteins, regulatory proteins, toxin proteins, cytokines, transcriptional regulatory factors, glucagon, blood coagulation factors, vaccines, enzyme inhibitors, a GNRH antagonist, insulin, human growth hormone, erythropoietin, filgrastin, heparin, low-molecular-weight heparin, and somatotropin.

An example of such vaccines may include any one selected from the group consisting of Japanese encephalitis vaccine sensitive to low temperature and temperate, rotavirus vaccine, influenza vaccine, polio vaccine, varicella vaccine, Alzheimer's disease vaccine, arteriosclerosis vaccine, cancer vaccine, nicotine vaccine, diphtheria vaccine, tetanus vaccine, mumps vaccine, cervical cancer vaccine, meningococcal vaccine, pertussis vaccine, Lyme disease vaccine, rabies vaccine, pneumococcal vaccine, yellow fever vaccine, cholera vaccine, vaccine exanthem, tuberculosis vaccine, rubella vaccine, measles vaccine, mumps vaccine, botulism vaccine, herpes virus vaccine, other DNA vaccines, hepatitis A or B vaccine, canine influenza vaccine, laptocephalosis, parainfluenza vaccine, infectious vaccine, and the like. That is, the active ingredient includes at least one of various ingredients to treat not only humans but also animals.

Meanwhile, the water-soluble substance that may be included in the coating agent C is preferably at least one of trehalose, oligosaccharide, sucrose, maltose, lactose, cellobiose, hyaluronic acid, alginic acid, pectin, carrageenan, chondroitin sulfate, dextran sulfate, chitosan, polylysine, collagen, gelatin, carboxymethyl chitin, fibrin, agarose, polyvinylpyrrolidone (PVP), polyethylene glycol (PEG), polymethacrylate, hydroxypropyl methyl cellulose (HPMC), ethyl cellulose (EC), hydroxypropyl cellulose (HPC), carboxymethyl cellulose, cyclodextrin, and gentiobiose.

Figure 4:
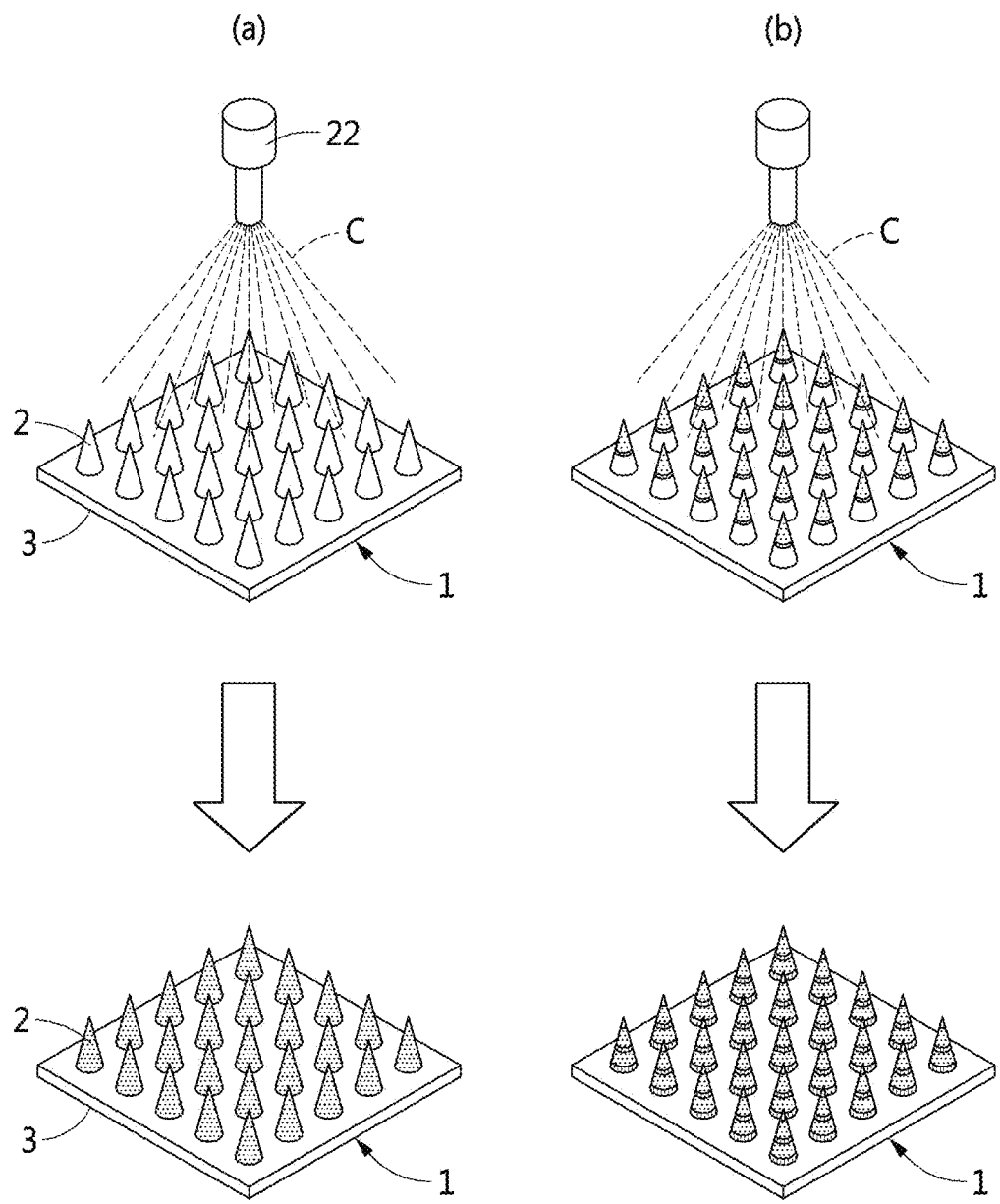
FIG. 4 is a drawing schematically illustrating the coating step illustrated in FIG. 1.

FIG. 4 schematically illustrates a method of spray-coating the cooled microneedle 1. As illustrated in FIG. 4, when the coating agent C is sprayed onto the microneedle 1 by a sprayer 22, the coating agent C is dissolved or coated on the microneedle 1. For reference, (a) of FIG. 4 illustrates a state wherein the coating agent C is dissolved and coated on the microneedle 1, and (b) of FIG. 4 illustrates a state wherein the coating agent C is coated on the tips 2.

Here, as illustrated in (b) of FIG. 4, the coating agent C coated on the tips 2 is preferably coated to an upper part of the microneedle 1, i.e., up to one fifth or more of the height from end portions of the tips 2. The microneedle 1 is dried in a state wherein the coating agent C is dissolved and coated on the microneedle 1 as illustrated in (a) and (b) of FIG. 4, thereby finally manufacturing the microneedle 1.

Although not illustrated in detail, in the coating step 30, the microneedle 1 may be coated, in a multilayer structure, with two or more drugs having the same solubility. That is, in the coating step 30, the microneedle 1 may be coated with the coating agent C including an active ingredient in multiple layers, i.e., at least once, by repeating a coating process as illustrated in FIG. 4.

For reference, the active ingredient included in the coating agent C is provided in a liquid state based on water and a solvent, and has a ratio of 0.1% to 90% based on the chemical liquid 13. Here, the active ingredient is preferably included in a ratio of 0.1% to 30%. In addition, the cooling step 20 and the coating step 30 are performed preferably under a relative humidity of less than 50%, more preferably 1% to 30%, under a vacuum or dry air condition. In addition, the coating step 30 is preferably performed under a humidity of 1% or more and less than 20%.

When the microneedle 1 is coated with the active ingredient sequentially through the cooling step 20 and the coating step 30 as described above, a separate drying process is unnecessary. In addition, although the microneedle 1 is coated with a substance having the same solubility as the microneedle 1 when the microneedle 1 is a meltable microneedle, a problem that the microneedle 1 and the substance are adhered to each other and, accordingly, end portions of the tips 2 become blunt and mechanical strength is decreased may be addressed.

Meanwhile, in the cooling step 20 for the microneedle 1 according to the embodiment, a cooling method, such as rapid cooling at −196° C. using liquid nitrogen, cooling at −78° C. using dry ice, cooling at −50 using tetrafluoroethane, or cooling at −20° C. using a Peltier element cooling fan, may be used.

In the waterproof coating step 40, a solvent is evaporated from the microneedle 1 coated with the coating agent C including the active ingredient, and the microneedle 1 is waterproof-coated such that the coated surface is not affected by a solution. In the waterproof coating step 40, the microneedle 1, i.e., end portions or entire surfaces of the tips 2, is coated with a waterproofing agent 31 including a mineral-based substance or a lipid-based material (see FIG. 5) by at least one of a dip-coating method, an atomization coating method, an electro-spinning coating method, and an ultrasonic coating method.

Here, the waterproofing agent 31 preferably includes at least one of beeswax, oleic acid, soy fatty acid, castor oil, phosphatidylcholine, vitamin E (d-α-tocopherol/vitamin E), corn oil mono-di-tridiglycerides, cottonseed oil, olive oil, peanut oil, peppermint oil, safflower oil, sesame oil, soybean oil, hydrogenated vegetable oils, hydrogenated soybean oil, capric triglycerides (caprylic/capric triglycerides derived from coconut oil or palm seed oil) and phosphatidylcholine, or is preferably formed of a mixture thereof.

Figure 5:
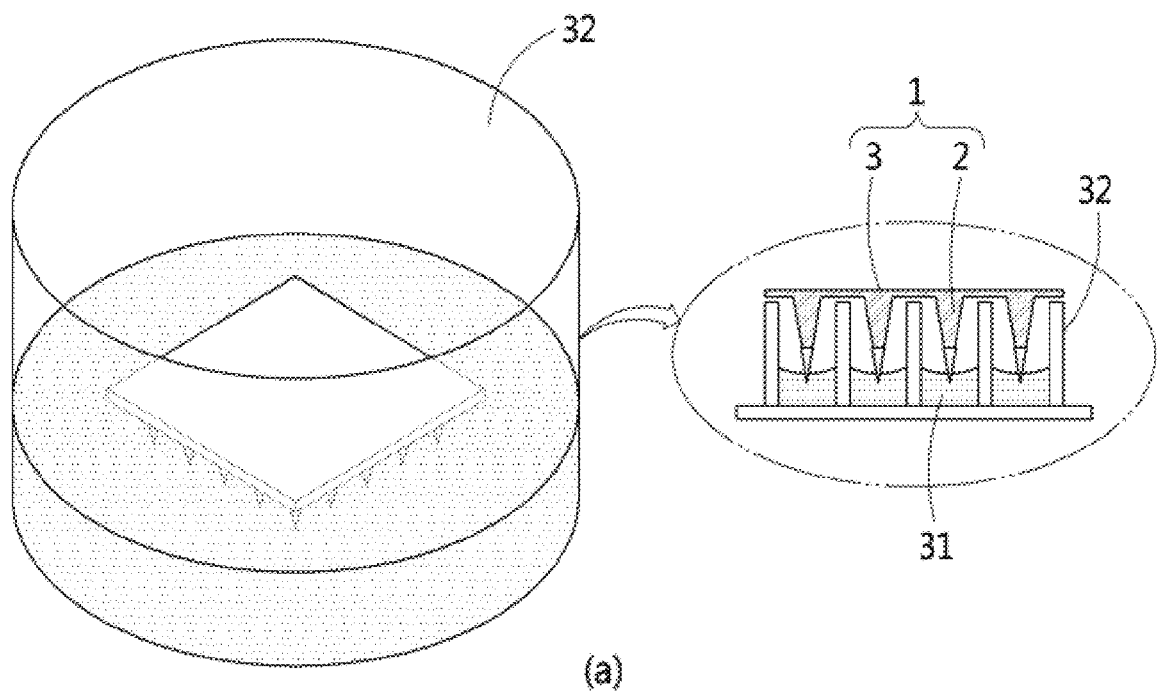
FIG. 5 is a drawing schematically illustrating a modified embodiment of the coating step illustrated in FIG. 4; and (a) of FIG. 6 illustrates a photograph of a microneedle manufactured by a conventional method, and (b) of FIG. 6 illustrates a photograph of a microneedle manufactured according to an embodiment of the present disclosure.
Figure 5:
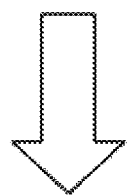
Figure 5:
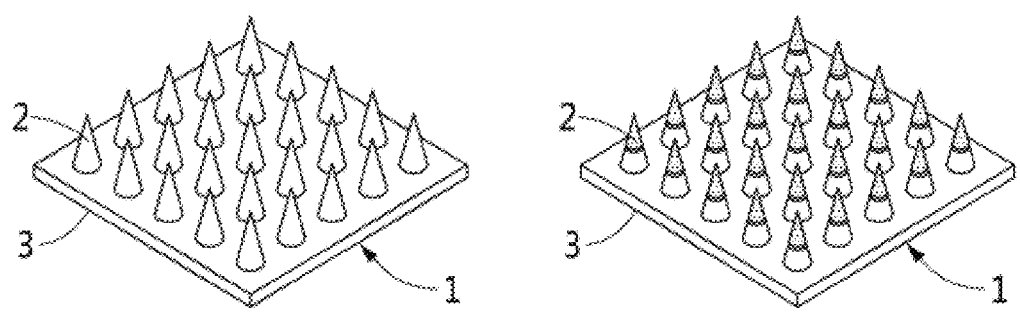

Referring to FIG. 5, a waterproof coating process performed in the waterproof coating step 40 is schematically illustrated. As illustrated in FIG. 5, the waterproofing agent 31 is contained in a waterproof chamber 32, and at least a portion of the microneedle 1 is immersed in the waterproofing agent 31 and thus waterproof-coated therewith. Here, (a) of FIG. 5 schematically illustrates the microneedle 1 on which the waterproofing agent 31 is dissolved and coated, and (b) of FIG. 5 schematically illustrates the microneedle 1 surface-coated with the waterproofing agent 31.

In the waterproof coating step 40, the microneedle 1 may be waterproof-coated with the waterproofing agent 31 prepared by an ethanol, as a solvent, with ~3 mg/ml of beeswax, ~32.5 mg/ml of cholesterol, ~550 mg/ml of phosphatidylcholine, ~210 mg/ml of palmitic acid, ~450 mg/ml of lauric acid, and ~70 mg/ml of stearic acid. In addition, in the waterproof coating step 40, the waterproofing agent 31 including 170 mg/ml of a palmitic acid solution may be used. In the waterproof coating step 30, the microneedle 1 sensitive to water is uniformly surface-coated in an electro-spraying method or an immersion method as illustrated in FIG. 5, followed by being dried at room temperature.

Figure 6:
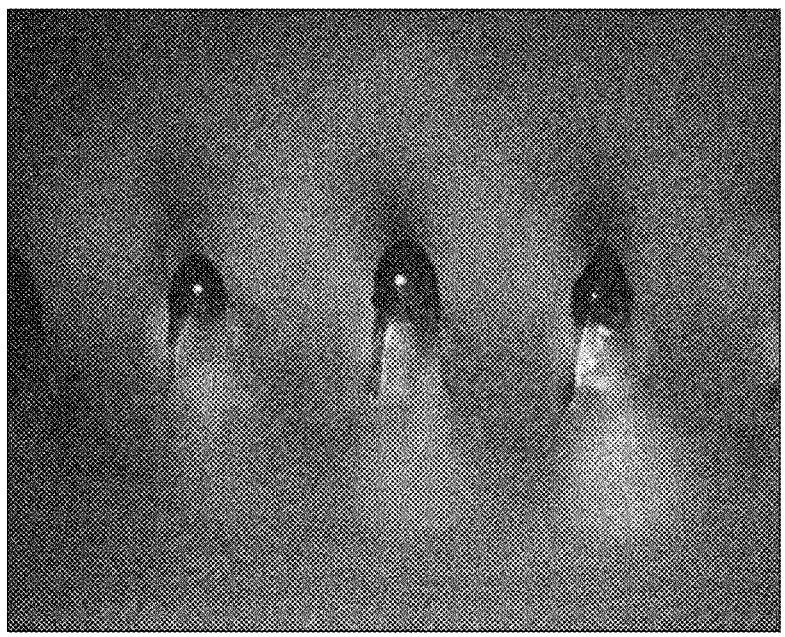
Figure 6:
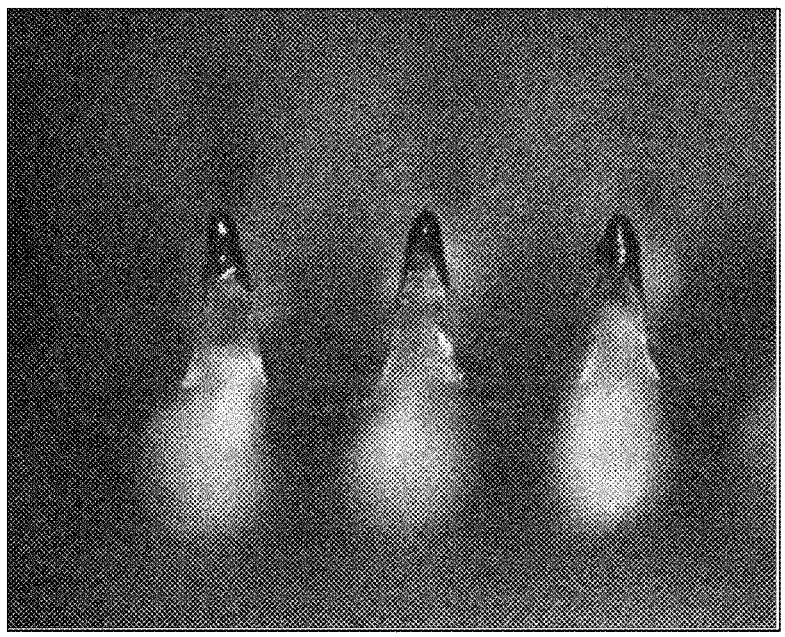

Referring to FIG. 6, (a) of FIG. 6 illustrates a state of a microneedle according to a conventional technology, and (b) of FIG. 6 illustrates a microneedle coated with the active ingredient through the cooling step 20 according to the embodiment of the present disclosure. As illustrated in FIG. 6, it can be confirmed that end portions of the microneedle 1 according to the embodiment of the present disclosure are coated with an active ingredient in superior quality while maintaining a pointed shape allowing easy penetration.

In accordance with the present disclosure having the aforementioned configuration, first, a conventional drying process of coating an active ingredient is unnecessary by coating a microneedle with an active ingredient after cooling the microneedle, whereby a manufacturing process becomes rapid and simple.

Second, since the microneedle is coated after being cooled, an endothermic reaction of the microneedle is induced, whereby solubility of an active ingredient is improved and thus superior medication is provided.

Third, since the microneedle and a substance coated thereon are not bound to each other even when the coated substance has the same solubility as the microneedle, it is advantage to maintain mechanical strength of the microneedle.

While the present invention has been described referring to the preferred embodiments of the present invention, those skilled in the art will appreciate that many modifications and changes can be made to the present invention without departing from the spirit and essential characteristics of the present invention.

DESCRIPTION OF SYMBOLS

1: Microneedle
2: Tip
3: Base
11: Mold
12: Tip groove
13: Chemical liquid
21: Cooling chamber
31: Waterproofing agent
32: Waterproof chamber

What is claimed is:

1. A method of manufacturing a microneedle, the method comprising:
   preparing a water-soluble microneedle;
   cooling the water-soluble microneedle;
   coating the cooled water-soluble microneedle with a water-soluble active ingredient at least once;
   after the cooled water-soluble microneedle is coated with the water-soluble active ingredient, waterproof-coating the microneedle with a waterproofing agent including a mineral-based substance or a lipid-based material; and
   drying the waterproof coated microneedle at a room temperature,
   wherein the cooling and the coating are sequentially performed under a vacuum or dry air condition without a separate drying process of the cooled water-soluble microneedle, a relative humidity in the cooling is 1% to 30%, and a relative humidity in the coating is 1% to 20%,
   wherein the cooling the water-soluble microneedle includes placing the water-soluble microneedle in a sealed cooling chamber and cooling the water-soluble microneedle while the water-soluble microneedle is placed in the sealed cooling chamber, wherein in the cooling, the microneedle is cooled by at least one rapid cooling method of a screw method, a piston method, a mono-pump method, a time-pressure method, a valve method, a spray method, a piezo method, an air-solenoid method, and an immersing the microneedle in a cooling substance, the cooling substance being at least one of liquid nitrogen, tetrafluoroethane, a Peltier element cooling fan, dry ice, wherein in the coating, the water-soluble microneedle is coated with the active ingredient by one of an electro-spinning coating method, an ultrasonic coating method, an atomization coating method, and a non-contact spray coating method, wherein in the coating, the water-soluble microneedle is coated, in a multilayer structure, with two or more active ingredients having same solubility, wherein in the waterproof-coating, an end portion or entire surface of the microneedle is coated with the waterproofing agent including the mineral-based substance or the lipid-based material by at least one of a dip-coating method, an atomization coating method, an electro-spinning coating method, and an ultrasonic coating method, and wherein the waterproofing agent includes at least one of beeswax, oleic acid, soy fatty acid, castor oil, phosphatidylcholine, vitamin E (d-α-tocopherol/Vitamin E), corn oil mono-di-tridiglycerides, cottonseed oil, olive oil, peanut oil, peppermint oil, safflower oil, sesame oil, soybean oil, hydrogenated vegetable oils, hydrogenated soybean oil, capric triglycerides (caprylic/capric triglycerides derived from coconut oil or palm seed oil) and phosphatidylcholine.

2. The method according to claim 1, wherein the preparing comprising:

preparing a mold having a plurality of tip grooves;

supplying a chemical liquid comprising at least a portion of a raw material or a biodegradable polymer ingredient to the mold to mold the microneedle; and removing the mold from the microneedle.

3. The method according to claim 2, wherein the mold comprises a polydimethylsiloxane (PDMS) mold and at least one of polyurethane, a metal, a biocompatible aluminum material, a water-soluble polymer, a lipophilic polymer, and an amphiphilic polymer, wherein the lipophilic polymer and the amphiphilic polymer comprise at least one of hydroxypropyl cellulose (HPC), hydroxypropyl methyl cellulose (HPMC), polycaprolactone (PCL), polyglycolide (PGA), polylactic acid (PLA), a polylactide-glycolide (PLGA) copolymer, polyvinylpyrrolidone (PVP), polyethylene glycol (PEG), polyethylene oxide (PEO), polypropylene oxide (PPO), poly(vinyl methyl ether) (PVME), poly(methyl acrylate) (PMA), propylene glycol, polyesteramide, polybutyric acid, acrylamide (acrylic amide), acrylic acid, hyaluronic acid (HA), and gelatin.

4. The method according to claim 2, wherein, in the supplying, the microneedle is molded through centrifugation and a polymer melting process after injecting the chemical liquid comprising the raw material in a low or high viscosity state into the mold.

5. The method according to claim 2, wherein the chemical liquid is formed of a biocompatible material and a water-soluble additive.

6. The method according to claim 5, wherein the biocompatible material comprises at least one of carboxymethyl cellulose (CMC), hyaluronic acid (HA), alginic acid, pectin, carrageenan, chondroitin sulfate, dextran sulfate, chitosan, polylysine, carboxymethyl chitin, fibrin, agarose, pullulan, polyanhydride, polyorthoester, polyetherester, polyesteramide, polybutyric acid, poly(valeric acid), polyacrylate, an ethylene-vinyl acetate polymer, acryl-substituted cellulose acetate, polyvinyl chloride, polyvinyl fluoride, polyvinyl imidazole, chlorosulphonate polyolefins, polyethylene oxide, polyvinylpyrrolidone (PVP), hydroxypropyl methyl cellulose (HPMC), ethyl cellulose (EC), hydroxypropyl cellulose (HPC), carboxymethyl cellulose, cyclodextrin, maltose, lactose, trehalose, cellobiose, isomaltose, turanose, and lactulose, or one or more of a copolymer of monomers forming this polymer and cellulose.

7. The method according to claim 6, wherein the water-soluble additive comprise at least one of trehalose, oligosaccharide, sucrose, maltose, lactose, cellobiose, hyaluronic acid, alginic acid, pectin, carrageenan, chondroitin sulfate, dextran sulfate, chitosan, polylysine, collagen, gelatin, carboxymethyl chitin, fibrin, agarose, polyvinylpyrrolidone (PVP), polyethylene glycol (PEG), polymethacrylate, hydroxypropyl methyl cellulose (HPMC), ethyl cellulose (EC), hydroxypropyl cellulose (HPC), carboxymethyl cellulose, cyclodextrin, and gentiobiose.

8. The method according to claim 1, wherein, in the coating, the active ingredient is coated up to one fifth or more of a height of the microneedle from an upper end of the microneedle.

9. The method according to claim 1, wherein, in the coating, a coating agent comprising a thickening agent, a biodegradable polymer resin, a water-soluble substance, and an active ingredient to be delivered to skin tissue is used.

10. The method according to claim 9, wherein the thickening agent comprises at least one of locust bean gum, rennet casein, dammer resin, glucosamine, glucomannan, guar gum, ghatti gum, carbomer, povidone, glycerin, carboxymethyl cellulose (CMC), hyaluronic acid, alginic acid, pectin, carrageenan, chondroitin sulfate, dextran sulfate, alginic acid, chitosan, karaya gum, polylysine, carboxymethyl chitin, fibrin, agarose, pullulan, polyanhydride, gellan gum, chitin, polyorthoester, microfibrillated, furcelleran, tragacanth gum, polyetherester, polyester amide, polybutyric acid, curdlan, polyvaleric acid, xanthan gum, polyacrylate, an ethylene-vinyl acetate polymer, acryl-substituted cellulose acetate, polyvinyl chloride, polyvinyl fluoride, tara gum, arabic gum, polyvinyl imidazole, psyllium seed gum, chlorosulphonate polyolefins, polyethylene oxide, polyvinyl pyrrolidone (PVP), chlorosulphonate polyolefins, hydroxypropyl methyl cellulose (HPMC), ethyl cellulose (EC), hydroxypropyl cellulose (HPC), carboxymethyl cellulose, cyclodextrin, maltose, lactose, trehalose, cellobiose, isomaltose, turanose, and lactulose, or at least one of a copolymer of monomers forming this polymer and cellulose.

11. The method according to claim 1, wherein the active ingredient comprises at least one of α-interferon, β-interferon related to multiple sclerosis, interferon gamma, interleukin-1 alpha and beta, interleukin-3, interleukin-4, interleukin-6, interleukin-2, erythropoietin, follitropin β, follitropin α, G-CSF, GM-CSF, human chorionic gonadotropin, signal transduction proteins, adherent proteins, luteinizing hormone, salmon calcitonin, glucagon, structural proteins, regulatory proteins, toxin proteins, cytokines, transcriptional regulatory factors, glucagon, blood coagulation factors, vaccines, enzyme inhibitors, a GNRH antagonist, insulin, human growth hormone, erythropoietin, filgrastin, heparin, low-molecular-weight heparin, and somatotropin.

12. The method according to claim 9, wherein the water-soluble substance is at least one of trehalose, oligosaccharide, sucrose, maltose, lactose, cellobiose, hyaluronic acid, alginic acid, pectin, carrageenan, chondroitin sulfate, dextran sulfate, chitosan, polylysine, collagen, gelatin, carboxymethyl chitin, fibrin, agarose, polyvinylpyrrolidone (PVP), polyethylene glycol (PEG), polymethacrylate, hydroxypropyl methyl cellulose (HPMC), ethyl cellulose (EC), hydroxypropyl cellulose (HPC), carboxymethyl cellulose, cyclodextrin, and gentiobiose.

13. The method according to claim 1, wherein the microneedle comprises a plurality of tips having a conical shape or a polygonal pyramid shape.

14. The method according to claim 1, wherein the method further includes evaporating a solvent from the coated microneedle.

* * * * *